United States Patent [19]

Boehmer

[11] 4,217,289

[45] Aug. 12, 1980

[54] PROCESS FOR PURIFICATION OF THE ALKALI METAL SALT OF SULFONATED UNSATURATED ALIPHATIC CARBOXYLIC ACID

[75] Inventor: Matthew A. Boehmer, Allen Park, Mich.

[73] Assignee: BASF Wyandotte Corporation, Wyandotte, Mich.

[21] Appl. No.: 25,645

[22] Filed: Mar. 30, 1979

[51] Int. Cl.$^2$ .................. C07C 143/90; C09F 5/10
[52] U.S. Cl. ............................. 260/400; 260/419; 260/428.5; 562/580; 562/581
[58] Field of Search ............... 260/400, 419, 428.5; 562/580, 581

[56] References Cited

U.S. PATENT DOCUMENTS

| 2,316,719 | 4/1943 | Lyman | 260/400 |
| 2,743,288 | 4/1956 | Rueggeberg et al. | 260/400 |

OTHER PUBLICATIONS

Bailey's Industrial Oil and Fat Products, Swern, 3rd Ed. (1964) p. 902.

Primary Examiner—John F. Niebling

Attorney, Agent, or Firm—Bernhard R. Swick

[57] ABSTRACT

A process for purifying a salt of sulfonated unsaturated aliphatic carboxylic acid, and in particular, a salt of sulfonated oleic acid wherein unreacted saturated fatty acid impurities are removed by the steps of diluting the mixture of the salt of sulfonated acid and impurities with an amount of water sufficient to provide an aqueous solution containing from about 5 to about 30 percent by weight of the salt, adding a synthetic aliphatic or isoparaffinic hydrocarbon solvent having a boiling point in the range of about 150° C. to about 260° C. in an amount such that the hydrocarbon is present in about 10 to about 50 percent by volume, agitating the mixture for a time sufficient to provide an intimate contact of the solvent with the impurities, holding the mixture in a quiescent state for a time sufficient to allow the water and solvent to separate into layers, and then drawing off the purified aqueous layer. The aqueous layer thus extracted is preferably used in detergent formulations suitable for cleaning containers that will contact food, and the purified salt of oleic acid or the like provides improved products for use in this and other applications.

10 Claims, No Drawings

PROCESS FOR PURIFICATION OF THE ALKALI METAL SALT OF SULFONATED UNSATURATED ALIPHATIC CARBOXYLIC ACID

BACKGROUND OF THE INVENTION

1. Field of the Invention

The present invention relates to a process for purification of the alkali metal salt of sulfonated unsaturated aliphatic carboxylic acid, and more particularly, to an efficient extraction process whereby unreacted fatty acid impurities are separated from the sulfonated carboxylic acid salt.

2. Description of the Prior Art

Sulfonated unsaturated aliphatic carboxylic acids are well known, and the commercial process for production thereof is given in U.S. Pat. No. 2,743,288, issued Apr. 24, 1956. Theses salts of sulfonated unsaturated carboxylic acids have found use in the detergent industry, and the sodium salt of sulfonated oleic acid is particularly valuable. However, the commercial products generally contain a certain amount of impurities such as unreacted saturated fatty acids. These acids cause insoluble precipitates in formulated acid-type sanitizers such as in the formulation described in U.S. Pat. No. 3,650,954 and the disclosure of this patent is incorporated by reference herein. The fatty acids are particularly troublesome when the sanitizer is utilized at low temperatures, because the impurities then precipitate out, and the precipitate even remains when the sanitizer solution is returned to room temperature.

At the time of the invention, the closest known prior art was U.S. Pat. No. 2,743,288 wherein the production of the sodium salt of sulfonated oleic acid and the like is disclosed. In the patent, purification by extraction is suggested, but it is stated that, for most purposes, extraction is unnecessary because of the small amount of unreacted materials in the product. A typical extraction process is disclosed in Example 1 wherein the product is extracted with three separate extractions of petroleum ether. As disclosed in the patent, considerable impurities are removed in the second and third extractions and the extracted material is primarily stearic acid. Accordingly, it is seen that the extractions suggested by the patentee are not commercially suitable for purification of the product.

Other techniques have been tried for the removal of unreacted fatty acid impurities such as, precipitation by cooling, followed by filtration. However, none of these other techniques have been commercially satisfactory.

SUMMARY OF THE INVENTION

It has now been found that the alkali metal salts of sulfonated unsaturated aliphatic carboxylic acids containing saturated fatty acid impurities can be purified by a commercially feasible extraction process wherein certain process parameters are observed. First of all, it is critical to the process of this invention to first dilute the salt of sulfonated oleic acid or the like with an amount of water sufficient to provide an aqueous solution containing from about 5 to about 30 percent by weight of the salt. It is also considered important to utilize an isoparaffinic hydrocarbon solvent having a high boiling point. Other advantageous process features such as achieving the purification in a single extraction step, effecting extraction contact under heated conditions, and utilizing pure solvents are also described more fully herein. Certain of these process parameters are necessary to provide the desired purification in a straight forward commercially acceptable manner, and certain other process parameters are important providing a purified product which will meet the government requirements for use in a sanitizer in the food industry.

Thus, in its broad aspect, the invention provides a process for purifying the salt of sulfonated unsaturated aliphatic carboxylic acid containing fatty acid impurities which comprises the steps of diluting the mixture with salt of sulfonated acid and impurities with an amount of water sufficient to provide an aqueous solution containing from about 5 to about 30 percent by weight of the salt of sulfonated unsaturated aliphatic carboxylic acid, adding an isoparaffinic hydrocarbon solvent having a boiling point in the range of from about 150° C. to about 260° C. in an amount such that the hydrocarbon is present in about 10 to about 50 percent by volume, agitating the mixture for a time sufficient to provide an intimate contact of the solvent with the impurities, holding the material in a quiescent state for a time sufficient to allow the water and solvent to separate into layers, and drawing off the aqueous layer.

Preferably, the solvent and mixture is agitated at a temperature of about 50° C. to about 95° C. to achieve a more efficient extraction, and the process is preferably carried out at in a single extraction step. It is also preferred to use a high purity, odorless, mineral spirit prepared from refinery process synthesis gas. The invention also provides for removal of solvent remaining in the separated aqueous phase and concentration of the salt, if desired. In particular, the invention provides a purified aqueous solution suitable for use in a sanitizer formulation meeting the government requirements for use in the food industry.

DESCRIPTION OF THE PREFERRED EMBODIMENTS

The products to be purified in accordance with the invention are those monosulfonated carboxylic acids described in U.S. Pat. No. 2,743,288 cited above and insofar as the patent disclosure is material to this invention, it is hereby incorporated by reference. The invention is particularly applicable, however, to the sodium salt of sulfonated oleic acid. It will be appreciated that when such sulfonated acids are produced, impurities result primarily from the impurity of the reactants utilized in the process. For example, when oleic acid is to be sulfonated, the product oleic acid frequently contains a certain amount of unsaturated acids such as stearic acid. These unsaturated acids then do not sulfonate according to the process of the cited patent and remain along with a product material as impurity. Accordingly, the amount of such impurities will vary considerably from one commercial batch to another. It is therefore necessary to provide a process which will remove a substantial amount of the impurity so that batches with considerable impurity will be adequately purified as well as those batches which contain relatively small amounts of impurity to start with.

In the patent described above, 50 percent aqueous solutions of the sodium salt of sulfonated oleic acid were extracted with petroleum ether. It has now been found, however, that one of the reasons for the inefficient extraction obtained by the patentee is the use of a 50 percent aqueous solution. Thus, in accordance with the invention, it is critical to utilize a solution which is diluted with water so that not more than 30 percent by weight of the salt of sulfonated oleic acid is present in the solution to be extracted, and preferably, the amount of salt will not exceed 20 percent by weight. On the other hand, aqueous solutions having amounts as low as 5 percent may be extracted although it is preferred to have at least about 8 percent salt in the aqueous solution.

The nature of the solvent to be utilized is also rather important. Not only is it important to utilize a good solvent for extraction efficiency, but it is also important to utilize a solvent that will not dissolve to any appreciable extent in the aqueous product phase. It has been found that the isoparaffinic hydrocarbon solvents having a boiling point in the range of about 150° C. to about 260° C. provide an efficient extraction with only a very small amount of the solvent remaining in the aqueous phase. In view of the fact that one of the important uses of the purified product is in the formulation of a sanitizer to be used in the food industry, it is also important to utilize a hydrocarbon solvent having especially good purity. Accordingly, it is preferred to use a high purity, odorless, mineral spirit prepared from refinery process synthesis gas. It has been found that when such solvents are utilized in accordance with the invention, the solvent remaining in the separated aqueous phase is present in an amount less than 0.05 percent by weight. However, if this amount of hydrocarbon solvent is still too high, it may be reduced by steam stripping so as to be present in an amount less than 0.02 percent by weight.

When the preferred water dilution and heated contact time is used, rather efficient extractions may be effected with lower boiling hydrocarbon solvents. However, it will be appreciated that the use of such materials, particularly when heated, renders the process more expensive because of the handling of hazardous materials. In addition, lower boiling hydrocarbons tend to dissolve to a greater extent in the aqueous salt solution, and this means that they should be removed to obtain a commercial product. Therefore, it is desirable to use higher molecular weight, pure, hydrocarbon solvents that have a low solubility in the aqueous salt solution, and a flash point correspondingly easier to work with on an industrial scale.

In carrying out the extraction process, it is also desirable to agitate the mixture of aqueous salt solution in hydrocarbon solvent at a temperature of say about 60° C. to about 95° C. for a time sufficient to provide an intimate contact to the solvent with the impurities. It has been found that this higher temperature provides a better removal of impurities in the extraction process, and thereby provides a more efficient extraction. In fact, it is a major feature of this invention that the extraction carried out herein is efficient enough to remove sufficient impurities in a single extraction step.

After the mixture has been agitated, it is held in a quiescent state for a time sufficient to allow the water and solvent to separate into layers. In general, the time for complete separation will be of the order of say about 9 hours. After separation, the aqueous solution bottom layer is simply removed from the mixing vessel by use of a bottom valve and transparent hose by conventional liquid separating techniques.

The purified product, although diluted with water, is suitable for use in making a sanitizer such as that described in U.S. Pat. No. 3,650,954. However, if desired, the solution may be concentrated by evaporation of water, or it may be stripped with steam to remove any trace solvent therein.

The invention described above is illustrated by the following specific examples, in which parts are by weight unless otherwise specified. The examples are to be interpreted as illustrative only, and not in a limiting sense.

EXAMPLE 1

A 1000 gallon agitated, jacketed mixing vessel with a dished bottom and bottom discharge valve was charged first with 335 gallons of tap water. The main mixer was started and the steam turned on to heat the water. During the heating, 110 gallons of Sulfonate OA-5 was added. Sulfonate OA-5 is the trade designation of a 50 percent aqueous solution of the sodium salt of sulfonated oleic acid prepared by the procedure given in U.S. Pat. No. 2,743,288 and sold without removal of unreacted fatty acids. After about 10 minutes, the steam was turned off, and the solution was at a temperature of 146° F. 110 Gallons of Isopar ®M was added and the temperature of the mixture dropped to 132° F. Isopar ®M is the trade designation of a special synthetized isoparaffin of high quality sold by Exxon. It has a flashpoint of 180° F. (Pensky-Martens closed cup) and a distillation range of 400–480° F. with 430° F. being the boiling point at 50 percent distillation. The second mixer was turned on for about 10 minutes to thoroughly agitate the heated liquid. After about five hours, a one quart sample was taken and 30 gallons of salt solution was drawn off. The rest of the liquid was allowed to sit over the weekend, and the remainder of the salt solution was drawn off. A 15 foot, one inch I.D., transparent plastic hose was used to detect the interface and separate the liquid phases. Samples were also taken at the middle and end of the salt solution recovery.

When the separation was made, about four gallons of liquid at the interface was removed, and this liquid is either recycled or sent to disposal. Samples were analyzed to determine the amount of solvent in the salt solution. The amount was determined to be 0.19 percent.

A portion of the product salt solution was stripped by a laboratory steam distillation, and the resulting product contained 0.04 percent Isopar ®M solvent. It is believed similar results may be obtained by simply boiling off about 10 percent by volume of water from the salt solution. In any event, the purified salt solution may be concentrated back to the original 50 percent concentration by evaporation, if desired. This concentration will reduce the amount of hydrocarbon solvent considerably. However, certain products such as the sanitizer of U.S. Pat. No. 3,650,954 may be made with the dilute extracted solution, as shown in Example 2 below.

EXAMPLE 2

A low foam anionic acid sanitizer was made according to Example I-G of U.S. Pat. No. 3,650,954 using the purified sodium salt of sulfonated oleic acid obtained in Example 1. Specifically, the sanitizer was made by adding with mixing at 75° F. to 95° F. the following ingredients in the amounts and order given:

| Substance | Parts by Weight |
| --- | --- |
| Water | 45.5 |
| Purified Sodium Sulfonated Oleic Acid of Example 1 (25%) | 28.0 |
| Propylene Glycol | 5.0 |
| Phosphoric Acid, 75% | 21.0 |

| Substance | Parts by Weight |
|---|---|
| -continued | |
| Pluronic®L61* | 0.5 |
| | 100.0 |

*PLURONIC L61 is a commercial product of BASF Wyandotte Corporation. It is a polyoxyethylene-polyoxypropylene block copolymer having a molecular weight of about 2,000 and contains about 10 percent by weight of oxyethylene units.

Another batch of the above acid sanitizer was made using the same procedure and the same concentrations of ingredients except that the unpurified commercial sodium salt of sulfonated oleic acid was used.

Samples of each sanitizer were stored for two days at 34° F. The batch made with purified sodium salt of oleic acid had no precipitate, but the batch made with unpurified sodium salt of oleic acid had a ¼ inch layer of precipitate floating on top.

From these examples, it is seen that the impure sodium salt of sulfonated oleic acid may be purified in a single extraction step in an amount sufficient to prevent precipitation of impurities in products made therefrom under cold conditions.

EXAMPLE 3

A series of exploratory tests were made to determine the effectiveness of extraction under various conditions. In Table I below, the amounts of materials in parts by volume and operating parameters are shown for these tests.

Table I

| Test | a | b | c | d | e | f |
|---|---|---|---|---|---|---|
| OA-5 | 75 | 50 | 50 | 50 | 30 | 30 |
| H$_2$O | 0 | 50 (RT) | 50 (hot) | 50 (hot) | 60 (RT) | 60 (hot) |
| Solvent | 50 | 25 | 25 | 25 | 25 | 25 |
| Separation | poor | good | good | good | good | good |

In all of the tests except (d), the solvent was SC140, and in test (d), it was odorless mineral spirits. In test (a) where the OA-5 (commercial 50 percent aqueous solution of the sodium salt of sulfonated oleic acid) was not diluted with additional water, separation was poor and the extraction was considered a failure. In all the other tests, at least some purification was obtained. The OA-5 of samples (b–e), thus purified, was then tested for fatty acid impurities by adding 80 milliliters cold water to 20 milliliters of test sample, and holding the test solution at about 37° F. for 42 hours. The appearance of these samples are given in Table II below.

Table II

| Sample | b | c | d | e | f |
|---|---|---|---|---|---|
| Appearance After Cooling | slight haze | slight haze | slight haze | cloudy white | clear |
| Appearance After Cooling & Rewarming Overnight | slight haze | haze | haze | white layer on top | clear |
| After Rewarming | drops | drops | droplets | white layer on top | clear |

From Table II above, it is seen that the dilution of the OA-5 should be as in test f rather than in tests (b), (c) and (d). Comparison of Test (e) and (f), however, show that hot extraction should also be used. Accordingly, these data shows that the recommended operating parameters of this invention are needed to obtain excellent purification in a single extraction.

The embodiments of the invention in which an exclusive property or privilege is claimed are defined as follows:

1. A process for purifying a salt of sulfonated unsaturated aliphatic carboxylic acid containing fatty acid impurities which comprises the steps of
   diluting the mixture of the salt of sulfonated acid and impurities with an amount of water sufficient to provide an aqueous solution containing from about 5 to 30 percent by weight of the salt of sulfonated acid,
   adding an isoparaffinic hydrocarbon solvent having a boiling point in the range of from about 150° C. to about 260° C. in an amount such that the hydrocarbon is present in about 10 to about 50 percent by volume,
   agitating the mixture for a time sufficient to provide an intimate contact of the solvent with the impurities,
   holding the material in a quiescent state for a time sufficient to allow the water and solvent to separate into layers, and
   drawing off the aqueous layer.

2. A process for purifying a salt of sulfonated unsaturated aliphatic carboxylic acid as defined in claim 1, wherein the solvent and the mixture are agitated at a temperature of from about 50° C. to about 95° C.

3. A process for purifying a salt of sulfonated unsaturated aliphatic carboxylic acid as defined in claim 1, wherein a major portion of the impurities are removed in a single extraction, whereby the desired process is achieved in one extraction.

4. A process for purifying a salt of sulfonated unsaturated aliphatic carboxylic acid as defined in claim 1, wherein the solvent is a high purity, odorless, mineral spirit prepared from refinery process synthesis gas.

5. A process for purifying a salt of sulfonated unsaturated aliphatic carboxylic acid as defined in claim 4, wherein the solvent remaining in the separated aqueous phase is present in an amount less than 0.20 percent by weight.

6. A process for purifying a salt of sulfonated unsaturated aliphatic carboxylic acid as defined in claim 5, wherein the separated aqueous phase is stripped with steam in an amount sufficient to reduce the solvent present to less than 0.04 percent by weight.

7. A process for purifying a salt of sulfonated unsaturated aliphatic carboxylic acid as defined in claim 1, wherein the separated water layer is concentrated by evaporation of water therefrom.

8. A process for purifying a salt of sulfonated oleic acid containing fatty acid impurities which comprises the steps of
   diluting the mixture of the salt of sulfonated oleic acid and impurities with an amount of water sufficient to provide an aqueous solution containing from about 8 to about 20 percent by weight of the salt of sulfonated oleic acid,
   adding an isoparaffinic hydrocarbon solvent having a boiling point in the range of about 150° C. to about 260° C. in an amount such that the hydrocarbon is present in about 15 to about 30 percent by volume,
   agitating the mixture at a temperature of from about 60° C. to about 95° C. for a time sufficient to provide an intimate contact of the solvent with the impurities, holding the material in a quiescent state for a time sufficient to allow the water and solvent to separate into layers, and removing the water layer from the solvent layer.

9. A process for purifying a salt of sulfonated oleic acid as defined in claim 8 wherein the separated aqueous phase is stripped with steam to remove residual solvent therein.

10. A process for purifying a salt of sulfonated unsaturated aliphatic carboxylic acid as defined in claim 8, wherein the separated water layer is concentrated by evaporation of water therefrom.